(12) United States Patent
Borsari et al.

(10) Patent No.: US 12,336,624 B2
(45) Date of Patent: Jun. 24, 2025

(54) BRUSH OR SWAB ASSEMBLY AND METHOD OF MANUFACTURING A BRUSH OR SWAB

(71) Applicant: SANDERSON MACLEOD, INC., Palmer, MA (US)

(72) Inventors: Mark Borsari, Wilbraham, MA (US); Chris Tarling, Southport, CT (US)

(73) Assignee: Sanderson Macleod, Inc., Palmer, MA (US)

( * ) Notice: Subject to any disclaimer, the term of this patent is extended or adjusted under 35 U.S.C. 154(b) by 638 days.

(21) Appl. No.: 17/533,498

(22) Filed: Nov. 23, 2021

(65) Prior Publication Data

US 2022/0160117 A1    May 26, 2022

Related U.S. Application Data (60) Provisional application No. 63/117,512, filed on Nov. 24, 2020.

(51) Int. Cl.
| | | |
|---|---|---|
| A46B 3/18 | (2006.01) | |
| A46B 9/02 | (2006.01) | |
| A46D 3/00 | (2006.01) | |
| A61B 10/00 | (2006.01) | |
| A61F 13/38 | (2006.01) | |

(52) U.S. Cl.
CPC .............. *A46B 3/18* (2013.01); *A46B 9/026* (2013.01); *A46D 3/00* (2013.01); *A61B 10/0051* (2013.01); *A61F 13/385* (2013.01)

(58) Field of Classification Search
CPC ......... A46B 5/0037; A46B 3/18; A46B 9/026; A46D 1/0207; A46D 1/0238; A45D 40/262; A61B 10/0051
See application file for complete search history.

(56) References Cited

U.S. PATENT DOCUMENTS

| | | | |
|---|---|---|---|
| 1,825,929 A | 10/1931 | Voigt | |
| 1,967,597 A * | 7/1934 | Schwartz | ................. A46B 5/00 15/206 |
| 2,580,378 A | 8/1945 | Peterson et al. | |
| 2,633,592 A * | 4/1953 | Meyer | ...................... A46B 7/10 15/206 |

(Continued)

FOREIGN PATENT DOCUMENTS

| | | |
|---|---|---|
| EP | 1510149 | 3/2005 |
| GB | 2064314 | 6/1981 |

(Continued)

OTHER PUBLICATIONS

PCT International Search Report dated Mar. 16, 2022 from corresponding International Application No. PCT/US2021/60513 filed Nov. 23, 2021.

*Primary Examiner* — Michael D Jennings
(74) *Attorney, Agent, or Firm* — Grogan, Tuccillo & Vanderleeden, LLP (57) ABSTRACT

A swab includes a core wire section having a proximal end and a distal end, an integral tip formed on the distal end, and at least one sleeve element received on the core wire section. The at least one sleeve element has a layer of fibers covering the sleeve and disposed on the at least one sleeve element by flocking, the layer of fibers being configured to absorb a quantity of a specimen in the layer of fibers.

20 Claims, 5 Drawing Sheets

(56) References Cited

U.S. PATENT DOCUMENTS

| | | | |
|---|---|---|---|
| 3,582,140 A * | 6/1971 | Kaufman | A46B 3/18 15/206 |
| 3,613,664 A | 10/1971 | Willson et al. | |
| 3,998,235 A | 12/1976 | Kingsford | |
| 4,108,162 A | 8/1978 | Chikashige et al. | |
| 4,257,434 A | 3/1981 | Wahl | |
| 4,411,282 A | 10/1983 | Wavering | |
| 4,886,693 A * | 12/1989 | Haranoya | D02G 3/408 428/401 |
| 5,135,112 A | 8/1992 | Kamen et al. | |
| 6,260,558 B1 * | 7/2001 | Neuner | A46B 9/021 401/122 |
| 6,345,626 B1 | 2/2002 | Bouix | |
| 6,354,337 B1 | 3/2002 | Odessky et al. | |
| 6,374,450 B1 | 4/2002 | Aoyama | |
| 6,465,758 B1 | 10/2002 | Ham | |
| 6,591,842 B2 | 7/2003 | Gueret | |
| 6,691,716 B2 | 2/2004 | Neuner et al. | |
| 6,699,331 B1 | 3/2004 | Kritzler | |
| 6,717,092 B2 * | 4/2004 | Obata | A61B 10/06 219/127 |
| 6,823,552 B1 * | 11/2004 | Hillenbrand | A46B 3/18 15/106 |
| 6,920,662 B2 | 7/2005 | Moore | |
| 7,121,284 B2 | 10/2006 | Gueret | |
| 7,721,379 B2 | 5/2010 | Takahashi | |
| RE41,710 E | 9/2010 | Dumler et al. | |
| 8,136,536 B2 | 3/2012 | Bickford | |
| 8,091,562 B2 | 6/2012 | Manici et al. | |
| 8,850,650 B2 | 10/2014 | Borsari et al. | |
| 8,919,351 B1 | 12/2014 | Wang | |
| 9,066,573 B2 | 6/2015 | Pires et al. | |
| 9,232,851 B2 | 1/2016 | Manici | |
| 9,254,028 B2 * | 2/2016 | Gueret | A46D 1/0238 |
| 10,111,515 B2 * | 10/2018 | Kim | A46B 3/10 |
| 2003/0084913 A1 * | 5/2003 | Gueret | A46B 3/18 132/218 |
| 2003/0163884 A1 | 9/2003 | Weihrauch | |
| 2004/0158945 A1 | 8/2004 | Moore | |
| 2005/0060824 A1 * | 3/2005 | Hillenbrand | B08B 9/0436 15/206 |
| 2005/0060825 A1 * | 3/2005 | Hillenbrand | A46B 3/18 15/206 |
| 2005/0133056 A1 | 6/2005 | Montoli | |
| 2005/0172437 A1 | 8/2005 | Wachter | |
| 2006/0225760 A1 * | 10/2006 | Kearney | A46B 9/021 132/218 |
| 2008/0011317 A1 | 1/2008 | Malvar et al. | |
| 2008/0034524 A1 | 2/2008 | Takahashi | |
| 2008/0107470 A1 * | 5/2008 | Gueret | A46B 3/16 401/129 |
| 2010/0037911 A1 | 2/2010 | Kim | |
| 2010/0192320 A1 | 8/2010 | Borsari et al. | |
| 2010/0319720 A1 | 12/2010 | Thorne et al. | |
| 2011/0282243 A1 | 11/2011 | Nakatani | |
| 2015/0313681 A1 * | 11/2015 | Eikens | A61B 1/122 15/104.05 |
| 2017/0215565 A1 | 8/2017 | Kamm | |
| 2017/0239026 A1 | 8/2017 | Kalbfeld et al. | |
| 2017/0258214 A1 * | 9/2017 | Borsari | A46B 9/026 |
| 2019/0350353 A1 * | 11/2019 | Borsari | A46D 1/0207 |
| 2019/0391051 A1 * | 12/2019 | O'Leary | A61B 10/02 |
| 2020/0288852 A1 * | 9/2020 | Borsari | A46B 13/003 |
| 2020/0367631 A1 * | 11/2020 | Bianco | A45D 40/265 |
| 2021/0102699 A1 * | 4/2021 | Bain | A47L 9/0693 |

FOREIGN PATENT DOCUMENTS

| | | |
|---|---|---|
| WO | 2009048244 | 4/2009 |
| WO | 2013034638 | 3/2013 |
| WO | 2015052607 A1 | 4/2015 |
| WO | 2016135270 | 9/2016 |

* cited by examiner

BRUSH OR SWAB ASSEMBLY AND METHOD OF MANUFACTURING A BRUSH OR SWAB

CROSS-REFERENCE TO RELATED APPLICATIONS

This application claims the benefit of U.S. Provisional Application Ser. No. 63/117,512, filed on Nov. 24, 2020, which is hereby incorporated by reference herein in its entirety.

FIELD OF THE INVENTION

The present invention relates generally to brushes and swabs and, more particularly, to a flocked brush or swab having a twisted wire core.

BACKGROUND OF THE INVENTION

Brushes have long been used for a variety of purposes including, for example, cleaning the interior surfaces of vessels and tubular bodies, collecting biological specimens or samples and applying personal care product compositions such as mascara. Brushes that are used for the collection of biological specimens may take a variety of forms, some of which may more accurately referred to as biological specimen collection swabs. These swabs are typically used in the collection of biological specimens of organic material for clinical and diagnostic analysis.

Existing swabs typically consist of a cylindrical rod or stem, the distal tip of which carries an absorbent material with hydrophilic properties to allow rapid absorption of the quantity of specimen to be collected and tested. For example, the absorbent material may be a wad of fiber such as rayon, or a natural fiber such as cotton. Stable adherence of the fiber wrapped around the tip of the rod is generally achieved by gluing. Other swabs have fibers disposed on the distal tip by flocking in an electrostatic field.

While existing swabs are suitable for what may be regarded as ordinary performance, there is a need for a flocked brush or swab that improves upon those that currently exist in the art.

SUMMARY OF THE INVENTION

In view of the foregoing, it is an object of the present invention to provide a brush or swab.

It is another object of the present invention to provide a swab for collecting a biological specimen.

It is another object of the present invention to provide a swab having a twisted wire core or stem.

It is another object of the present invention to provide a brush or swab having flocking on the tip and/or stem.

These and other objects are achieved by the present invention.

According to an embodiment of the invention, a swab includes a core wire section having a proximal end and a distal end, an integral tip formed on the distal end, and at least one sleeve element received on the core wire section. The at least one sleeve element has a layer of fibers covering the sleeve and disposed on the at least one sleeve element by flocking, the layer of fibers being configured to absorb a quantity of a specimen in the layer of fibers.

According to another embodiment of the invention, a swab includes a core wire section having a proximal end and a distal end, an integral tip formed on the distal end, and cap received on the integral tip. The cap has a layer of fibers covering the cap and disposed on the cap by flocking, the layer of fibers being configured to absorb a quantity of a specimen in the layer of fibers.

According to yet another embodiment of the invention, a swab includes a core wire section having a proximal end and a distal end, an integral tip formed on the distal end, and a layer of fibers covering the integral tip and disposed on the integral tip by flocking, the layer of fibers being configured to absorb a quantity of a specimen in the layer of fibers.

BRIEF DESCRIPTION OF THE DRAWINGS

The present invention will be better understood from reading the following description of non-limiting embodiments, with reference to the attached drawings, wherein below.

DETAILED DESCRIPTION OF THE PREFERRED EMBODIMENTS

Figure 1:
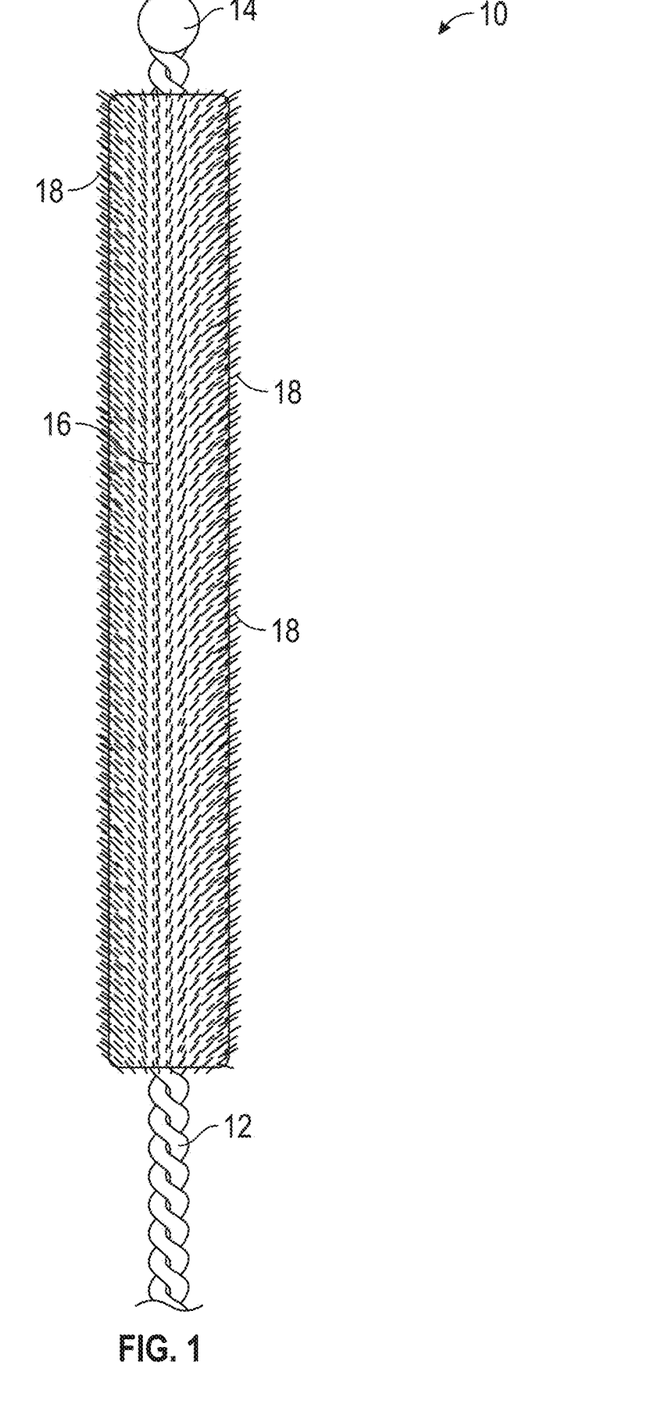
FIG. 1 is a side elevational view of a flocked swab according to one embodiment of the present invention.

Referring to FIG. 1, a brush 10, also referred to herein as swab 10, according to an embodiment of the present invention is illustrated. As shown therein, the swab 10 includes a core wire section 12 and a spherical or substantially round or ball-shaped tip 14 integrally formed with the core wire section 12 at a distal end thereof (such that the core wire section 12 and the tip 14 form a unitary part). In an embodiment, the swab or brush 10 may include a plurality of fibers or bristles (not shown) secured by the core wire section 12 and extending radially therefrom, as is known in the art.

In an embodiment, the core wire section 12 and the integral tip 14 may be fabricated in the manner disclosed in U.S. Pat. Nos. 8,850,650 and 8,783,787, which are hereby incorporated by reference herein in their entireties. In particular, the core wire section 12 is preferably formed from a pliable metallic wire that is reversibly folded back upon itself to form two generally coextensive leg portions, which are then twisted in a helical configuration (and retain bristles, where utilized). In an embodiment, the core wire section 12 may be comprised of nickel alloys, titanium alloys, stainless steel alloys, carbon steel alloys, cobalt alloys or aluminum alloys, although other metals or metal alloys may be used without departing from the scope of the present invention. While this is an exemplary method of forming a twisted in wire brush, it will be readily appreciated that any fabrication process or method for forming twisted in wire brushes known in the art may be employed, without departing from the scope of the present invention. For example, it will be readily appreciated that a plurality of wires may be used in place of the single wire described above. In such a situation, the plurality of wires may be placed adjacent one another, a plurality of bristles placed between the wires, and the wires twisted together to form a core of helical configuration and to anchor the bristles in place. Other methods and configurations of forming wire brushes and twisted in wire brushes are known in the art and may be incorporated in the current design without departing from the scope of the present invention. In an embodiment, the core wire section 12 may be a single length of wire (i.e., not a plurality of legs twisted about each other). In an embodiment, the core wire section 12 may anchor a plurality of fiber bristle elements, as disclosed in the patents indicated above.

As disclosed above, the distal end of the core wire section 12 is formed with an integral, substantially spherical tip or ball 14. The integral tip 14 may be formed on the distal end of the wire core by melting or welding only the distal end of the core section 12 after twisting of the core 12, as disclosed in U.S. Pat. Nos. 8,850,650 and 8,783,787. For example, to form the smooth and substantially rounded ball 14 on the distal end of the core wire section 12, high-energy fusion welding may be used to "melt" the core sire section 12 of the swab 10 at the distal end thereof.

Importantly, the core wire section 12 and the integral tip 14 are homogeneous, in that the tip 14 is made of existing material from the core wire section 12 without the addition of any other quantity of material. The tip 14, is therefore made to be consistent, smooth and inseparable from the core wire section 12. Melting the distal end of the core wire section 12 also melts and eliminates any sharp or uneven edges, and eliminates any contaminant trapping voids that may be present. Once fused, the coextensive leg portion of the wire core are unable to be separated from one another, and the rounded tip is also inseparable from the core wire section 12. Importantly, welding or melting of the distal end of the core wire section 12 results in a metallurgical bond between the enlarged tip 14 and the core wire section 12 of the brush 10, which increases the structural strength of the brush itself and aids substantially in ensuring that the leg portions of the core wire section 12 do not become unraveled.

Specific welding technologies such as Laser, Gas Tungsten Arc Welding (GTAW), Plasma Arc Welding and Electron Beam Welding may be used to melt/weld the distal end of the core wire section 12 to form the spherical tip 14. In particular, the preferred parameter range is 0.001 Milliamps to 200 Amps for Gas Tungsten Arc Welding, 15 Kv-200 Kv for Electron Beam Welding and 1 Amp-200 Amps for Plasma Arc Welding, although other parameters may be used. For Laser technology, near ultraviolet and/or near infra-red laser sources are preferred, although other wavelengths may be used to achieve the objects of the present invention. While the embodiments described herein disclose a spherical tip, in certain embodiments, the tip may be generally spherical (i.e., not entirely spherical).

With further reference to FIG. 1, in an embodiment, the swab 10 further includes a generally cylindrical sleeve 16 received about, and retained on, the core wire section 12. In particular, the cylindrical sleeve 16 may include an interior passageway through which the core wire section 12 extends. In an embodiment, the sleeve 16 may be formed from a plastic or polymer, although other materials known in the art may be utilized without departing from the broader aspects of the invention. The sleeve 16 may be formed via any process known in the art, such as molding, additive manufacturing processes, etc. The tip 14 preferably has a diameter that is larger than an inside diameter of the sleeve 16 such that the tip 14 functions as a position stop for the sleeve 16. In an embodiment, the sleeve 16 is covered with fibers 18 that are deposited on the sleeve 16 by flocking. The flocking technique is preferably of the type conducted in an electrostatic field which deposits the fibers in an ordered manner, perpendicular to the surface of the sleeve 16, which has been previously coated with adhesive, for example, by immersion or spraying. In an embodiment, the fibers 18 may be a layer of fibers. As used herein, "layer" is not intended to mean a continuous layer or to be interpreted as necessarily fully covering a certain component to which the fibers are applied.

In accordance with the objects of the invention, the fiber is chosen from a wide range of materials provided they are hydrophilic by capillarity, such as for example, synthetic or artificial materials e.g. rayon, polyester, polyamide, carbon fiber or alginate, natural materials e.g. cotton and silk, or mixtures thereof. In an embodiment, the fiber may be chosen from a wide range of materials provided they are hydrophilic by capillarity so as to allow for the absorption of biological specimens.

It is contemplated that the sleeve 16 may be flocked in an offline process, and then assembled onto the pre-constructed core wire section 12. Alternatively, it is envisioned that the sleeve 16 may be flocked after assembly onto the core wire section 12. Flocking the sleeve 16 offline, however, may allow for more customized flocking of the sleeve 16. It is further contemplated that instead of a single sleeve 16, a plurality of sleeve elements may be disposed on the core wire section 12. The sleeve elements may be formed with a plurality of fibers, bristles or the like (e.g., flocked fibers). In an embodiment, the sleeve elements may be flocked different from one another (e.g., certain of the sleeve elements may have different fibers, fiber density, fiber thickness, etc. than other sleeve elements).

In an embodiment, one or more of the sleeve elements may be formed as stacked disc elements as disclosed in U.S. patent application Ser. Nos. 16/817,973 and 16/818,052, which are hereby incorporated by reference herein in their entireties. The stacked disc elements may or may not be flocked.

Figure 2:
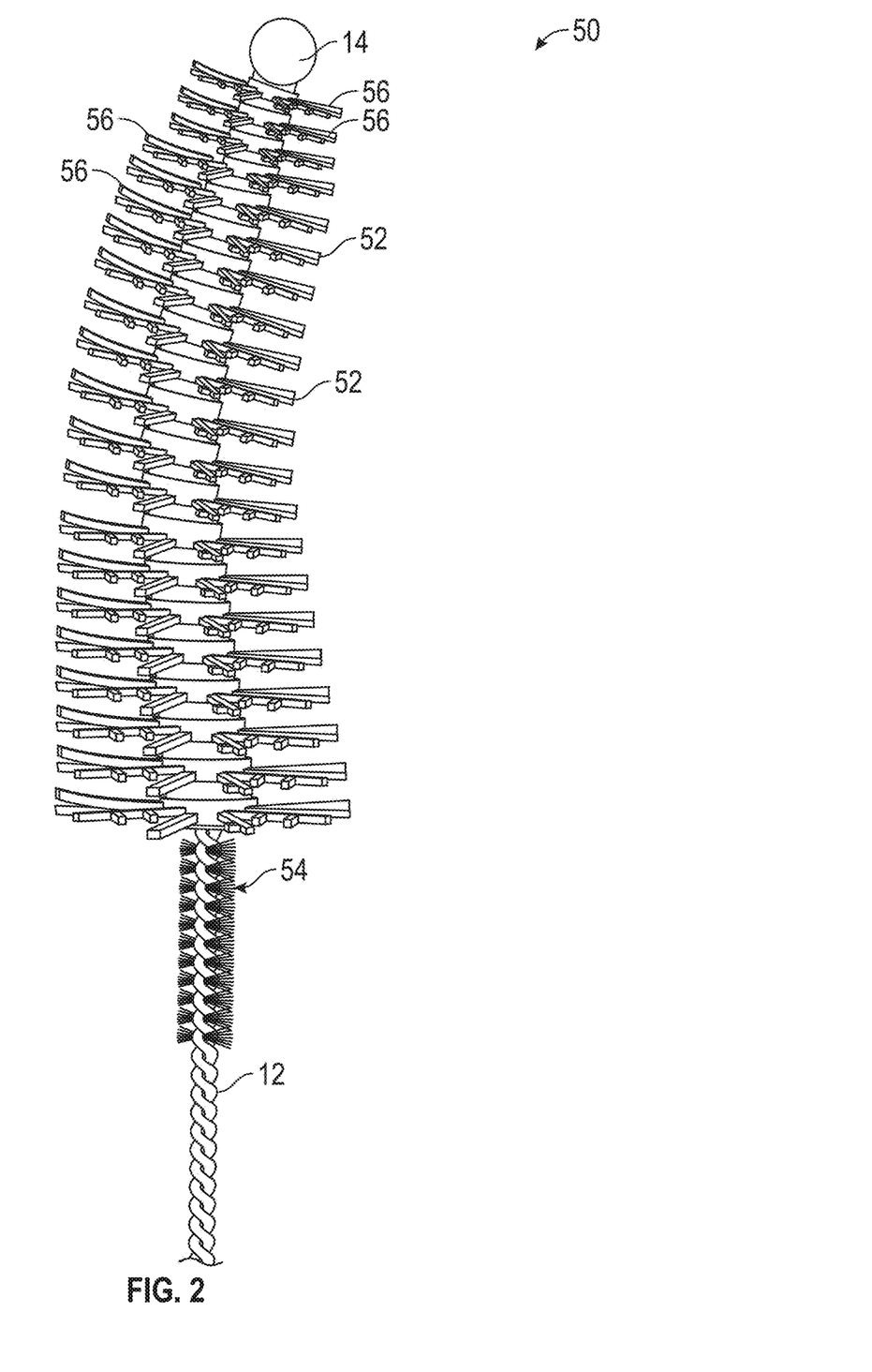
FIG. 2 is a side, cross-sectional view of a flocked swab according to another embodiment of the present invention.

With reference to FIG. 2, a swab 50 according to another embodiment of the invention is illustrated. The swab 50 is constructed similarly to swab 10, where like reference numerals designating like parts. Rather than having a single sleeve element, however, the swab 50 contains a plurality of sleeve elements in the form of stacked disc elements 52 received on the wire core section 12. As alluded to above, the stacked disc elements may or may not be flocked, although flocking is shown at 56. In either embodiment, the core wire section 12 may retain a plurality of fiber bristles 54, which may aid in retaining the sleeve element(s) or discs in position on the core wire section 12.

As will be appreciated, in either embodiment, by forming the sleeve as an array of sleeve elements with different fiber characteristics (e.g., type, density, thickness, etc.), the functional properties of the swab 10 may be more specifically tailored to its particular use and/or in dependence upon the anatomy of a subject from which a biological specimen is to be collected. In yet another embodiment, the swab may contain a single sleeve element such as that shown in FIG. 1, and different portions of the sleeve element may be flocked with materials having different characteristics.

In use, the swab may be utilized to collect biological specimens of organic material for clinical and diagnostic analysis. For example, in an embodiment, the swab may be a nasopharyngeal swab used for collecting a sample of organic material (e.g., nasal secretions) from the back of the nose and throat of a human subject.

Figure 3:
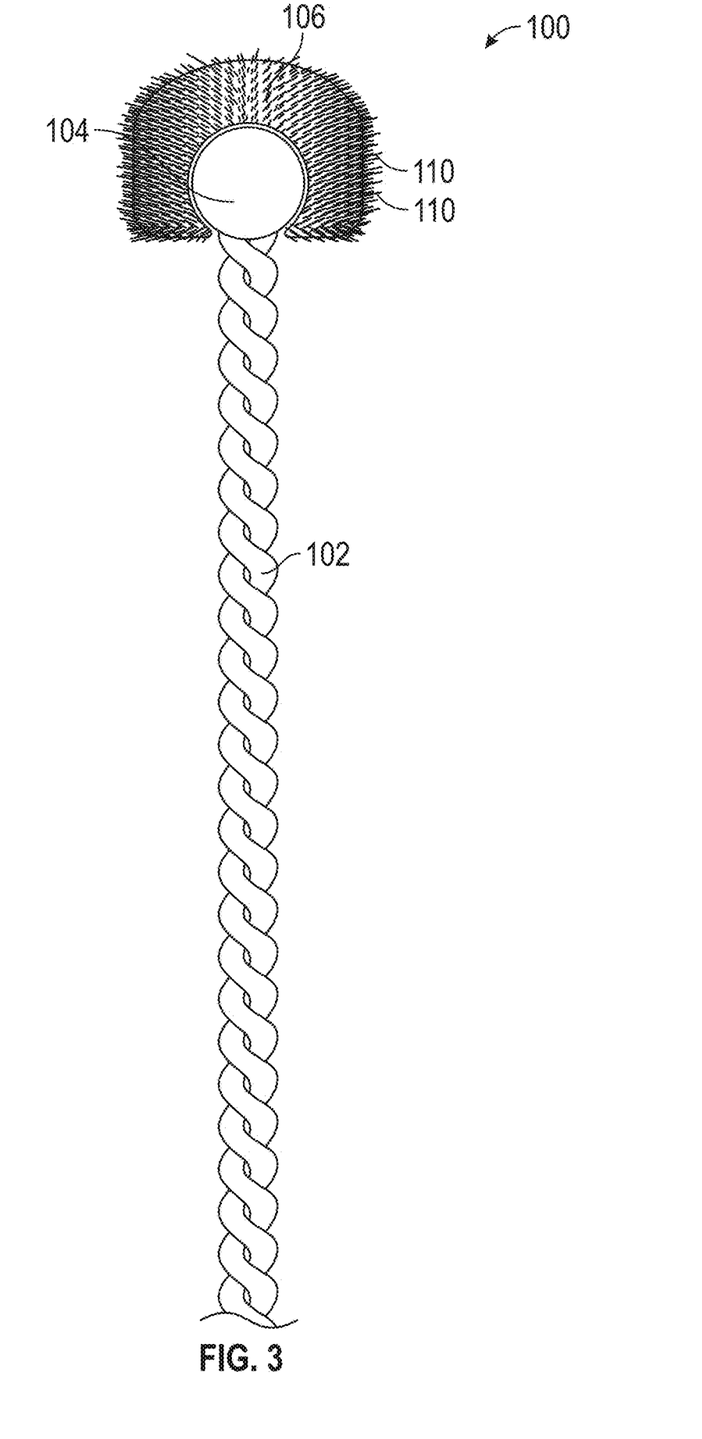
FIG. 3 is a side, cross-sectional view of a flocked swab according to another embodiment of the present invention.
Figure 4:
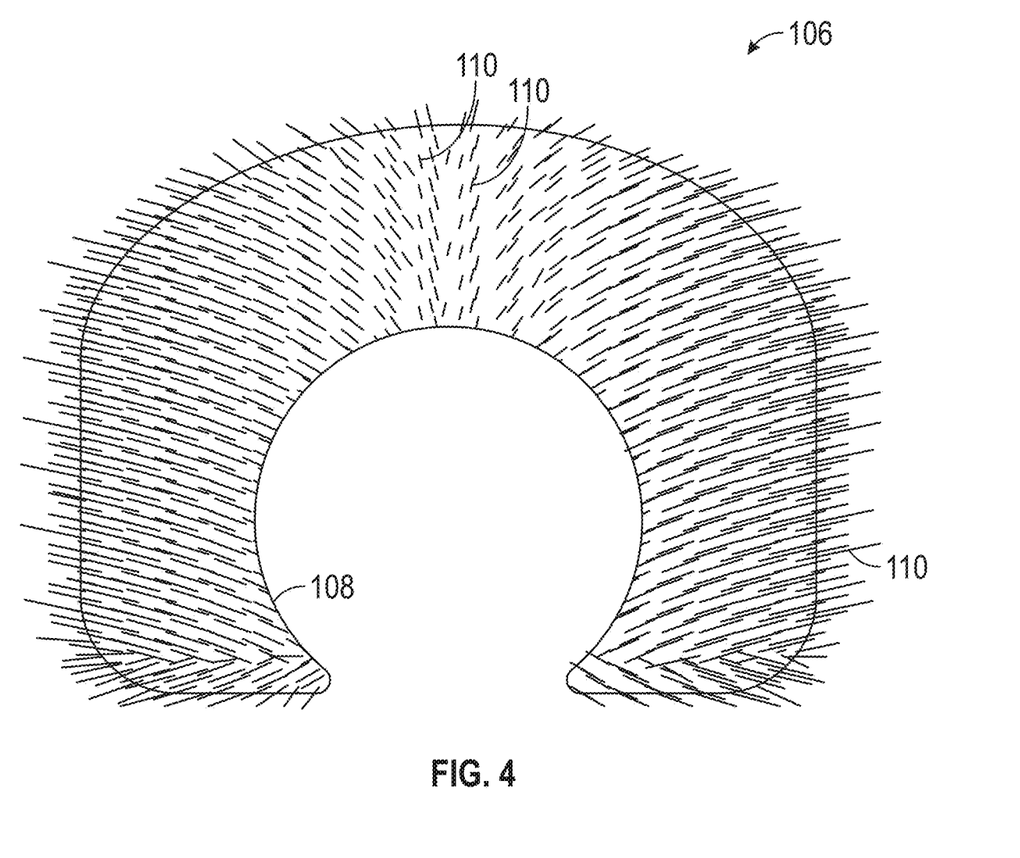
FIG. 4 is an enlarged, cross-sectional view of a flocked cap of the swab of FIG. 3.

Turning now to FIG. 3, a swab 100 according to another embodiment of the present invention is illustrated. As shown therein, the swab 100 includes a core wire section 102 and a spherical or substantially round or ball-shaped tip 104 integrally formed with the core wire section 102 at a distal end thereof, both of which are formed as disclosed above in connection with the embodiment of FIG. 1. As further shown in FIG. 3, the swab 100 includes a cap element 106 coupled to the spherical tip 104. For example, as best shown in FIG. 4, in an embodiment, the cap element 106 may have a socket 108 that generally corresponds in shape and size to the tip 104 so that the cap 106 and tip 104 may be connected to each other via a ball-and-socket connection (e.g., a snap fit connection. In other embodiments, the cap 106 may be over-molded onto the tip 104.

In an embodiment, the cap 106 may be formed from a plastic or polymer, although other materials known in the art may be utilized without departing from the broader aspects of the invention. The sleeve cap 106 may be formed via any process known in the art, such as molding, additive manufacturing processes, etc. Similar to the sleeve of FIG. 1, the cap 106 may have a plurality of fibers 110 disposed on an exterior surface thereof such as by flocking. The flocking technique is preferably of the type conducted in an electrostatic field which deposits the fibers in an ordered manner, perpendicular to the surface of the sleeve 16, which has been previously coated with adhesive for example by immersion or spraying.

In accordance with the objects of the invention, the fiber is chosen from a wide range of materials provided they are hydrophilic by capillarity, such as for example, synthetic or artificial materials, e.g., rayon, polyester, polyamide, carbon fiber or alginate, natural materials e.g. cotton and silk, or mixtures thereof.

It is contemplated that the cap 106 may be flocked in an offline process, and then assembled onto the tip 104. Alternatively, it is envisioned that the cap 106 may be flocked after assembly onto the tip 104.

Figure 5:
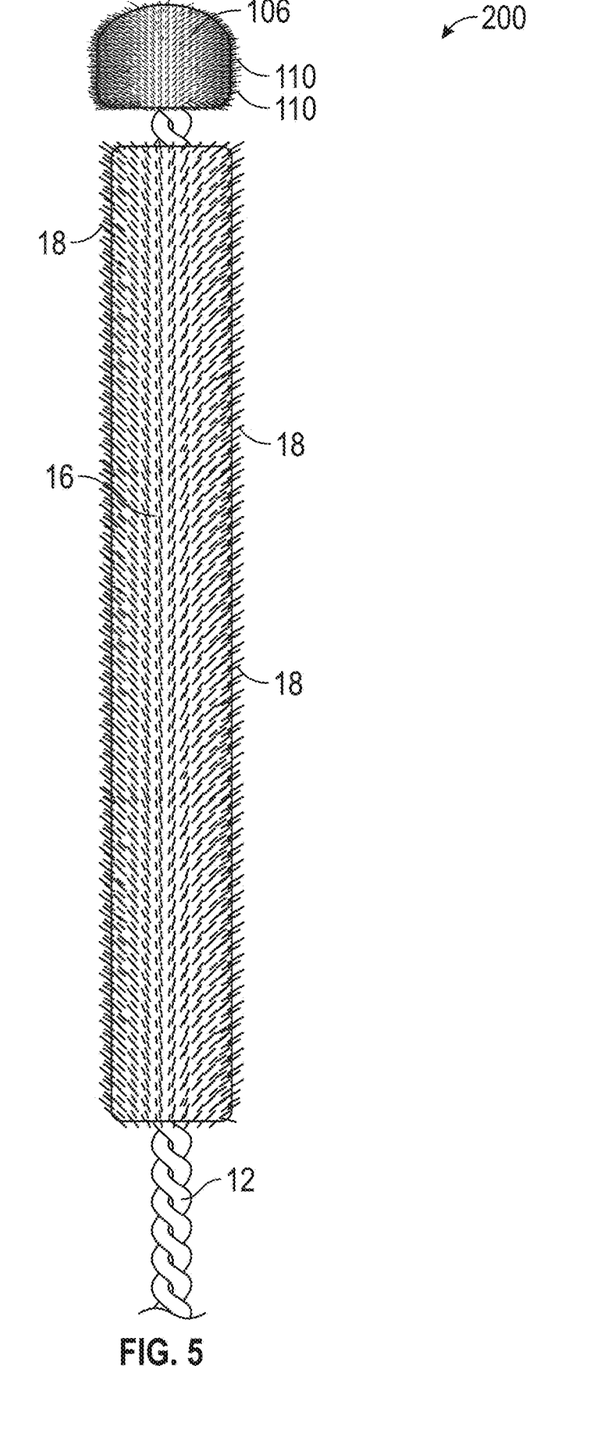
FIG. 5 is a side elevational view of a flocked swab according to another embodiment of the present invention.

As shown in FIG. 5, in yet another embodiment, it is contemplated that a swab 200 may include both a flocked sleeve 16 (or a plurality of discrete sleeve elements) received on the core wire section 12, and a flocked cap 106 received on the spherical tip. The flocking on the cap may have the same or different characteristics than the flocking on the sleeve (or sleeve elements). In still further embodiments, the core wire section, the integral tip of the swab, and/or the fiber bristles retained in the core wire section may be flocked directly (alternative to, or in addition to, flocking the sleeve and/or cap).

While it has been disclosed herein that the embodiments of the invention are particularly suited for use as a swab for collecting a biological specimen, the present invention is not so limited in this regard. In particular, it is envisioned that embodiments of the present invention may be utilized for a variety of end uses such as, for example, cleaning, application of personal care products such as mascara, and the like.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A swab, comprising:
   a core wire section having a proximal end and a distal end;
   an integral tip formed on the distal end; and
   at least one sleeve element having an interior passageway that is received over and retained on the core wire section, the at least one sleeve element having a layer of flocked fibers covering the sleeve element, the layer of flocked fibers being configured to absorb a quantity of a specimen in the layer of flocked fibers.

2. The swab of claim 1, wherein:
   the at least one sleeve element comprises a plurality of sleeve elements each having a layer of flocked fibers covering the sleeve elements.

3. The swab of claim 2, wherein:
   the layer of flocked fibers of at least one sleeve element of the plurality of sleeve elements has a characteristic that is different than the characteristic of the layer of flocked fibers of at least another of the plurality of sleeve elements.

4. The swab of claim 3, wherein:
   the characteristic is at least one of material type, thickness and/or density.

5. The swab of claim 1, further comprising:
   a cap received on the integral tip, the cap having a layer of flocked fibers covering the cap, the layer of flocked fibers being configured to absorb a quantity of a specimen in the layer of flocked fibers.

6. The swab of claim 5, wherein:
   the cap is connected to the integral tip via a ball-and-socket connection.

7. The swab of claim 1, wherein:
   the core section includes at least two leg members twisted about one another in a helical configuration.

8. The swab of claim 7, further comprising:
   a plurality of fiber bristles anchored in the core section.

9. The brush of claim 7, wherein:
   the integral tip and the core wire section each comprises a material that is homogeneous with one another.

10. The brush of claim 1, wherein:
    the at least one sleeve element comprises a plurality of stacked discs.

11. The swab of claim 1, wherein the at least one sleeve element with the layer of flocked fibers is separate and distinct from the core wire section.

12. A swab, comprising:
    a core wire section having a proximal end and a distal end;
    an integral tip formed on the distal end;
    at least one sleeve element having an interior passageway that is received over and retained on the core wire section, the at least one sleeve element having a layer of flocked fibers covering the sleeve element, the layer of flocked fibers on the sleeve element being configured to absorb a quantity of a specimen in the layer of fibers; and
    a cap received on the integral tip, the cap having a layer of flocked fibers covering the cap, the layer of flocked fibers on the cap being configured to absorb a quantity of a specimen in the layer of flocked fibers.

13. The swab of claim 12, wherein:
    the at least one sleeve element comprises a plurality of sleeve elements each having a layer of flocked fibers covering the sleeve elements.

14. The swab of claim 13, wherein:
    the layer of flocked fibers of at least one sleeve element of the plurality of sleeve elements has a characteristic that is different than the characteristic of the layer of flocked fibers of at least another of the plurality of sleeve elements.

15. The swab of claim 12, wherein:
the at least one sleeve element comprises a plurality of stacked discs, each of the plurality of stack discs having a layer of flocked fibers thereabout.

16. The swab of claim 12, wherein the at least one sleeve element with the layer of flocked fibers is separate and distinct from the core wire section.

17. A swab, comprising:
a core wire section having a proximal end and a distal end;
an integral tip formed on the distal end;
a layer of flocked fibers covering the integral tip, the layer of flocked fibers on the integral tip being configured to absorb a quantity of a specimen in the layer of flocked fibers; and
at least one sleeve element having an interior passageway that is received over and retained on the core wire section, the at least one sleeve element having a layer of flocked fibers covering the sleeve element, the layer of flocked fibers on the sleeve element being configured to absorb a quantity of a specimen in the layer of flocked fibers.

18. The swab of claim 17, wherein:
the integral tip and the core wire section each comprises a material that is homogeneous with one another.

19. The swab of claim 17, further comprising:
a plurality of fiber bristles anchored in the core wire section, wherein the plurality of fiber bristles are disposed in a location on the core wire section that is separated from the at least one sleeve element.

20. The swab of claim 17, further comprising a plurality of stacked discs extending axially along the core section to define a brush head, each of the stacked discs comprising a layer of flocked fibers disposed thereon.

* * * * *